United States Patent [19]

Abe et al.

[11] 4,172,016

[45] Oct. 23, 1979

[54] METHOD FOR MANUFACTURE OF PERFLUOROTETRAHYDROFURAN DERIVATIVES

[75] Inventors: Takashi Abe; Shunji Nagase, both of Nagoya, Japan

[73] Assignees: Agency of Industrial Science & Technology; Ministry of International Trade & Industry, both of Tokyo, Japan

[21] Appl. No.: 823,742

[22] Filed: Aug. 11, 1977

[30] Foreign Application Priority Data

Aug. 21, 1976 [JP] Japan .................................. 51-100096

[51] Int. Cl.² ............................................... C25B 3/08
[52] U.S. Cl. ................................................... 204/59 F
[58] Field of Search ........................................ 204/59 F

[56] References Cited

U.S. PATENT DOCUMENTS

| 2,594,272 | 4/1952 | Kauck et al. | 260/333 |
| 2,644,823 | 7/1953 | Kauck | 260/345.1 |

FOREIGN PATENT DOCUMENTS

| 1069639 | 11/1959 | Fed. Rep. of Germany . |
| 672720 | 5/1952 | United Kingdom . |
| 718318 | 11/1954 | United Kingdom . |
| 1007288 | 10/1965 | United Kingdom . |

*Primary Examiner*—R. L. Andrews
*Attorney, Agent, or Firm*—Kurt Kelman

[57] ABSTRACT

Perfluorotetrahyrofuran derivatives are produced by electrolytically fluorinating in hydrofluoric anhydride either monocarboxylic acids having a total of from 6 to 16 carbon atoms and possessing a side chain on the α carbon atom or derivatives thereof.

4 Claims, 7 Drawing Figures

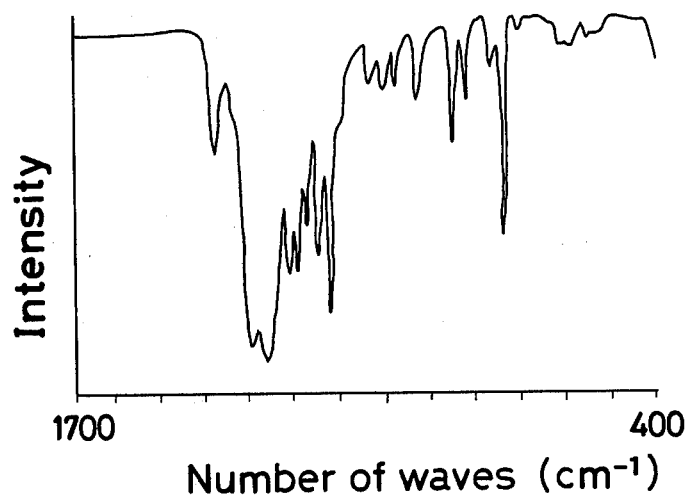
Fig_4
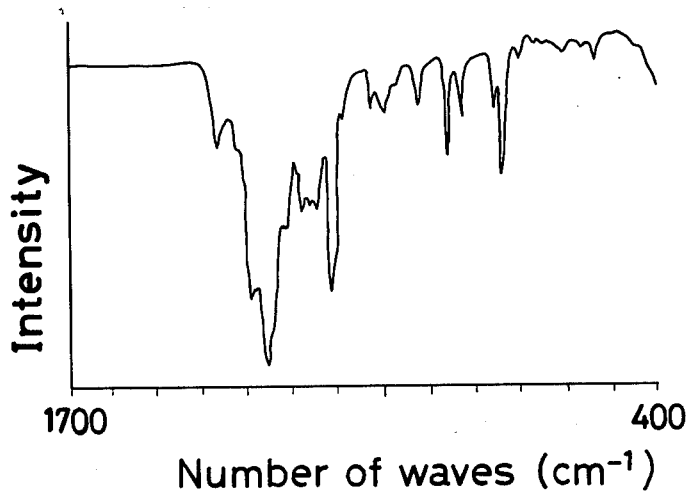
Fig_5

METHOD FOR MANUFACTURE OF PERFLUOROTETRAHYDROFURAN DERIVATIVES

BACKGROUND OF THE INVENTION

This invention relates to a method for the manufacture of novel perfluorotetrahydrofuran derivatives represented by the following generic formula.

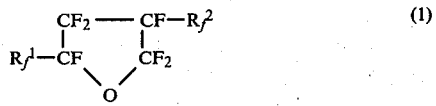

(wherein, $R_f^1$ stands for a fluorine atom or a straight-chain aliphatic perfluoroalkyl group having 1 to 7 carbon atoms and $R_f^2$ for a straight-chain aliphatic perfluoroalkyl group having 1 to 7 carbon atoms).

The compounds represented by the formula (1) are colorless, transparent, odorless liquids having extremely high thermal and chemical stability and are usable as solvents, solution media, etc. Heretofore, cyclic fluorinated ethers have been manufactured by various methods such as electrolytic fluorination of cyclic ethers (U.S. Pat. No. 2,594,272 and British Pat. No. 672,720), electrolytic fluorination of straight-chain carboxylic acids and derivatives thereof (U.S. Pat. No. 2,644,823, British Pat. No. 718,318, German Pat. No. 1,069,639 and French Pat. No. 1,636,296), electrolytic fluorination of alcohols (Japanese Patent Public Disclosure No. 123658/1975), electrolytic fluorination of aldehydes (Japanese Patent Publication No. 4,994/1976), etc. None of these methods relate in any way to such perfluoro-(2,4-dialkyltetrahydrofuran)s as are represented by the formula of (1) given above. Although German Pat. No. 1,069,639 is similar in some respects to the invention of this patent application in terms of raw material, product and method, it is different from this invention in that it necessitates use of an electric conduction agent and in other respects.

Heretofore, perfluoro-(2,4-dialkyltetrahydrofuran)s have been manufactured such as by electrolytic fluorination of monoalcohols having a side-chain group at the α position (represented by RCH₂OH, wherein R stands for a saturated or unsaturated, straight-chain or side-chain aliphatic alkyl group having 3 to 9 carbon atoms) (Japanese Patent Public Disclosure No. 88062/1975).

This method, however, has entailed a disadvantage that the electrolytic fluorination by-produces a large amount of a fluorocarbon having the same number of carbon atoms as the alcohol being used as the raw material and the separation of this by-product from the perfluoro-cyclic ether is difficult to carry out.

The inventors, in search of a method capable of producing perfluoro-(2,4-dialkyltetrahydrofuran)s of the aforementioned formula (1) by electrolytic fluorination, made an elaborate study of electrolytic fluorination of carboxylic acids and derivatives thereof. They have consequently made a discovery that the compounds of the aforementioned formula (1) are obtained in high yields by electrolytically fluorinating, under the conditions described hereinafter, carboxylic acids having side-chain groups particularly at the α position and derivatives thereof. They have accomplished this invention on the basis of this discovery.

An object of the present invention is to provide a method for the manufacture of perfluoro-(2,4-dialkyltetrahydrofuran)s by electrolytic fluorination.

SUMMARY OF THE INVENTION

To accomplish the object described above according to the present invention, there is provided a method for the manufacture of perfluorotetrahydrofuran derivatives represented by the generic formula (1):

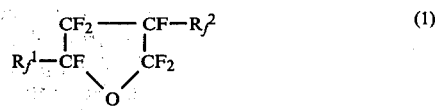

(wherein, $R_f^1$ stands for a fluorine atom or a straight-chain aliphatic perfluoroalkyl group having 1 to 7 carbon atoms and $R_f^2$ for an aliphatic perfluoroalkyl group having 1 to 7 carbon atoms) by electrolytically fluorinating, in hydrofluoric anhydride, monocarboxylic acids or halides, esters, amides and other similar derivative thereof represented by the generic formula (2):

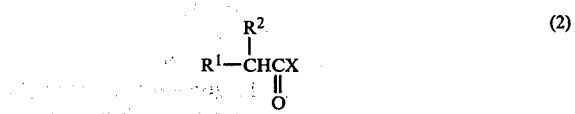

wherein, the α carbon possesses side chains, $R^1$ and $R^2$ each stand for a straight-chain aliphatic alkyl group having 1 to 7 carbon atoms, X stands for an OH group or a substituent to be described hereinafter, and the total number of carbon atoms falls in the range of from 6 to 16.

BRIEF DESCRIPTION OF THE INVENTION

FIGS. 4 and 5 are infrared absorption spectra of cis-perfluoro-(2-methyl-4-ethyltetrahydrofuran) and trans-perfluoro-(2-methyl-4-ethyltetrahydrofuran) which were the products in Example 2.

DETAILED DESCRIPTION OF THE INVENTION

Figure 1:
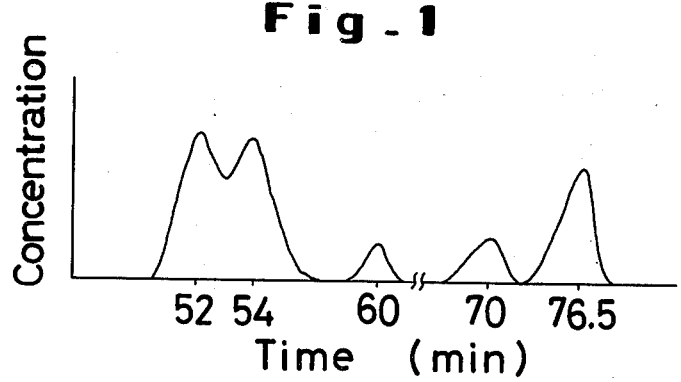
FIG. 1 is a gas chromatogram obtained of the fluorination product of Example 1.

First, monocarboxylic acids or derivatives thereof which are used in the present invention will be described.

In the present invention, there are used monocarboxylic acids or derivatives thereof represented by the generic formula:

wherein, (1) the α carbon possesses side chains, (2) $R^1$ and $R^2$ are each a straight-chain alkyl group having 1 to 7 carbon atoms, (3) X is one member selected from the class consisting of OH, halogen atoms, $R^3O$ [where $R^3$ is one member selected from the class consisting of methyl group and ethyl group], and $NH_2$ and (4) the total number of carbon atoms falls in the range of from 6 to 16.

The limited number of carbon atoms in the compound to be used as a raw material is determined by the structure of the particular perfluorotetrahydrofuran derivative aimed at. Judging from the usefulness of products, the upper limit of boiling points of products has been fixed at about 240° C. From this upper limit of boiling points, the upper limit of the total number of carbon atoms in the product has been fixed at 16.

Typical examples of monocarboxylic acids and derivatives thereof which are most advantageous for this invention are as follows:

(1) 2-methyl-n-valeric acid chloride
(2) 2-methyl-n-caproic acid chloride
(3) 2-methyl-n-enanthic acid chloride
(4) 2-ethyl-n-valeric acid methyl ester
(5) 2-n-propyl-n-valeric acid chloride
(6) 2-ethyl-n-caproic acid chloride
(7) 2-n-butyl-n-caproic acid methyl ester Generally, the electrolysis of a given monocarboxylic acid or derivative thereof is carried out with said acid or derivative dissolved in a large excess of hydrofluoric anhydride. The amount of said acid or derivative dissolved in the anhydride is from 5 to 20%, for example.

The electrolytic cell which used for this invention can be either of a horizontal type or of a vertical type, both of which are in common use now. In view of the electrolyte and the product involved, the material of the electrolytic cell is desirably against corrosion proof. Preferable examples of the material are monel metal and soft iron.

As the electrodes, use of an anode made of nickel and a cathode made of nickel or iron are desirable.

Now, the conditions under which the electrolysis is carried out will be described.

The optimum conditions are variable with the composition and concentration of the electrolyzate, the interval between the electrodes and the like. Generally, the cell voltage, bath temperature, and anodic current density must be fixed within their respective ranges shown below.

| | |
|---|---|
| Cell voltage | 4V to 8V |
| Bath temperature | 0° C. to 10° C. |
| Interval between electrodes | 1.7 mm to 2 mm |
| Anodic current density | 2.0 A/dm² to 4.0 A/dm² |

The substance indicated below which is aimed at by the present invention is produced by subjecting the raw material defined above to electrolysis under the conditions described above.

Specifically, the electrolysis gives rise to a principal component substance represented by the generic formula:

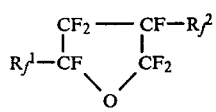

(1)

(wherein, $R_f^1$ stands for a fluorine atom or a straight-chain aliphatic perfluoroalkyl group having 1 to 7 carbon atoms and $R_f^2$ for a straight-chain aliphatic perfluoroalkyl group having 1 to 7 carbon atoms) in conjunction with by-products including a substance having perfluoroalkyl groups at positions other than the 2 and 4 positions in the aforementioned generic formula, perfluorocarboxylic acid fluoride corresponding to the raw material, fluorocarbons, hydrogen difluoride and carbonyl fluoride.

Typical examples of the perfluoro-(2,4-dialkyltetrahydrofuran)s to be produced by the method of this invention are enumerated below, together with their respective boiling points.

| | | |
|---|---|---|
| (1) | cis-perfluoro-(2,4-dimethyltetrahydrofuran) | 50.3 to 50.7° C. |
| (2) | trans-perfluoro-(2,4-dimethyltetrahydrofuran) | 51.1 to 51.6 |
| (3) | perfluoro-(3-ethyltetrahydrofuran) | 55.2 to 55.8 |
| (4) | cis-perfluoro-(2-ethyl-4-methyltetrahydrofuran) | 74.8 to 75.0 |
| (5) | trans-perfluoro-(2-ethyl-4-methyltetrahydrofuran) | 76.0 to 76.4 |
| (6) | cis-perfluoro-(2methyl-4-ethyltetrahydrofuran) | 75.4 to 75.7 |
| (7) | trans-perfluoro-(2-methyl-4-ethyltetrahydrofuran) | 75.5 to 76.0 |
| (8) | perfluoro-(2-methyl-4-n-propyltetrahydrofuran) | 95.5 to 95.7 |
| (9) | perfluoro-(2-ethyl-4-n-butyltetrahydrofuran) | 137.0 to 138.5 |

Of the compounds given in the preceding table, the first seven compounds [from (1) to (7)] are the perfluoro-(2,4-dialkyltetrahydrofuran)s which are produced by electrolytically fluorinating carboxylic acids having a total of 6 or 7 carbon atoms or derivative thereof and which have the substituents of $R_f^1=R_f^2=CF_3$, $R_f^1=R_f^2=CF_3$, $R_f^1=F$ and $R_f^2=C_2F_5$, $R_f^1=C_2F_5$ and $R_f^2=CF_3$, $R_f^1=C_2F_5$ and $R_f^2=CF_3$, $R_f^1=CF_3$ and $R_f^2=C_2F_5$, and $R_f^1=CF_3$ and $R_f^2=C_2F_5$ respectively. These are invariably liquids which are volatile at normal room temperature. They are obtained in the form of gaseous substances in conjunction with their respective perfluorocarboxylic acid fluorides, fluorocarbons, oxygen difluoride and carbonyl fluoride.

The isolation of the main reaction product from the byproducts is accomplished, for example, by a procedure comprising the steps of first introducing said gaseous reaction mixture into an iron tube packed with sodium fluoride pellets to be deprived of hydrogen fluoride, then passing the effluent from said iron tube through a gas scrubbing bottle packed with a mixed aqueous solution of potassium sulfite, potassium iodide and potassium hydroxide to effect removal therefrom of oxygen difluoride and carbonyl fluoride through absorption, and forwarding the residual gas to a trap cooled with liquefied nitrogen to be collected in said trap.

The last two compounds [(8) and (9)] are the perfluoro-(2,4-dialkyltetrahydrofuran)s which are obtained by electrolytically fluorinating carboxylic acids having a total of 8 to 16 carbon atoms or derivatives thereof and which have the substituents of $R_f^1=CF_3$ and $R_f^2=n-C_3F_7$, and $R_f^1=C_2F_5$ and $R_f^2=n-C_4F_{10}$. They have a total of 1 to 7 carbon atoms in the substituents $R_f^1$ and $R_f^2$ and are obtained in the form of liquid substances having boiling points in the range of from 95° to 240° C., and they are produced in conjunction with perfluorocarboxylic acid fluorides and fluorocarbons. These substances are formed in separate layers from the layer of hydrofluoric anhydride and, therefore, can easily be isolated. The perfluorotetrahydrofuran derivatives, perfluorocarboxylic acid fluorides and fluorocarbons are then distilled and further fractionated by fractional gas chromatography and are obtained in refined state.

The perfluorotetrahydrofuran derivatives obtained as described above are identified by mass spectrometry, infrared absorption spectrometry, $^{19}F$ nuclear magnetic resonance spectrometry and elementary analysis.

EXAMPLE 1

In a cylindrical electrolytic cell made of monel metal, having an inner volume of 1 liter, a diameter of 10 cm and a height of 21 cm, 8 nickel anodes each 5.5 cm in width, 15 cm in length and 0.5 mm in thickness and 9 cathodes of the same dimensions were alternately arranged at intervals of 1.7 to 2.0 mm. The total effective surface area of the anodes was 9.2 $dm^2$.

This electrolytic cell was provided with a reflux condenser. In the cell, 1 liter of hydrofluoric anhydride was placed and subjected to preliminary electrolysis with 35 A of current and 6 V of voltage to remove therefrom water and sulfuric acid. Then, 0.199 mol of 2-methyl-n-vareic acid chloride was dissolved in the hydrofluoric anhydride and the resultant mixture was subjected to electrolysis, while helium gas was blown in through the bubbler provided at the lower end of the electrolytic cell, with 3.5 A/$dm^2$ of anodic current density, 5° to 6° C. of bath temperature over a period of 141 A. hours until the voltage reached 10 V.

The gas formed by the electrolysis was first passed through an iron tube packed with sodium fluoride pellets to be deprived of hydrogen fluoride and then forwarded through a gas scrubber bottle containing a mixed aqueous solution of potassium sulfide, potassium iodide and potassium hydroxide to effect removal therefrom of hydrogen difluoride and carbonyl fluoride through absorption. The gas emanating from the scrubber bottle is led to a trap cooled with liquefied nitrogen and collected. The amount of the product thus collected was 8.84 g/h. The product was further purified by distillation. By analysis of the product by gas chromatography, mass spectrometry, infrared absorption spectrometry and $^{19}F$ nuclear magnetic resonance spectrometry it was ascertained that the treatment afforded 6.8 g (10.8% in yield) of cis-perfluoro-(2,4-dimethyltetrahydrofuran) (b.p. 50.3° to 50.7° C.) and 5.8 g (9.1% in yield) of trans-perfluoro-(2,4-dimethyltetrahydrofuran) (b.p. 51.1° to 51.6° C.) as products aimed at, in conjunction with 3.5 g (5.5% in yield) of perfluoro-(2-methyltetrahydropyran) and 6.5 g (10.4% in yield) of perfluoro-(3-methyltetrahydropyran) as perfluoro-cyclic ethers, plus 4.4 g (7.0% in yield) of perfluoro-(2-methyl-n-valeric acid fluoride) as a corresponding perfluorocarboxylic acid fluoride.

FIG. 1 represents a gas chromatographic chart obtained by using a column of 30% H(CF$_2$CF$_2$)$_2$CH$_2$O(CH$_2$)$_6$CH$_2$(CF$_2$CF$_2$)$_2$H on Chromosorb PAW with He as the carrier at 30° C. of temperature. In the chart, the vertical axis is graduated for concentration of component and the horizontal axis for lapse of time (in minutes). In the chart (30% HCC), the numerals:

1 represents cis-perfluoro-(2,4-dimethyltetrahydrofuran)
2 represents trans-perfluoro-(2,4-dimethyltetrahydrofuran)
3 represents perfluoro-(2-methyltetrahydropyran)
4 represents perfluoro-(2-methyl-n-valeric acid fluoride)
5 represents perfluoro-(3-methyltetrahydropyran).

Figure 2:
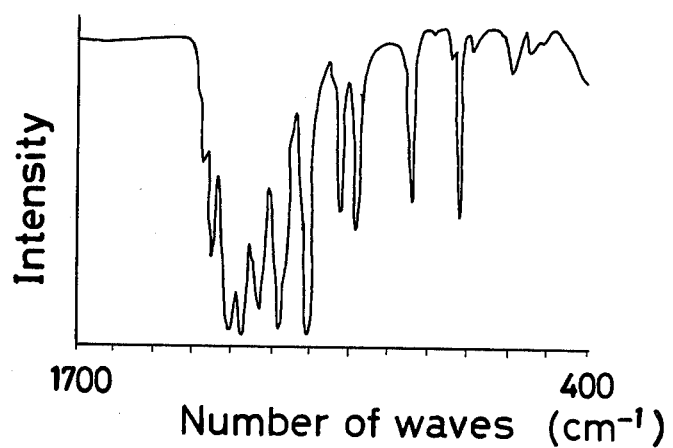
FIGS. 2 and 3 are infrared absorption spectra of cis-perfluoro-(2,4-dimethyltetrahydrofuran) and trans-perfluoro-(2,4-dimethyltetrahydrofuran) which were the products in Example 1.
Figure 3:
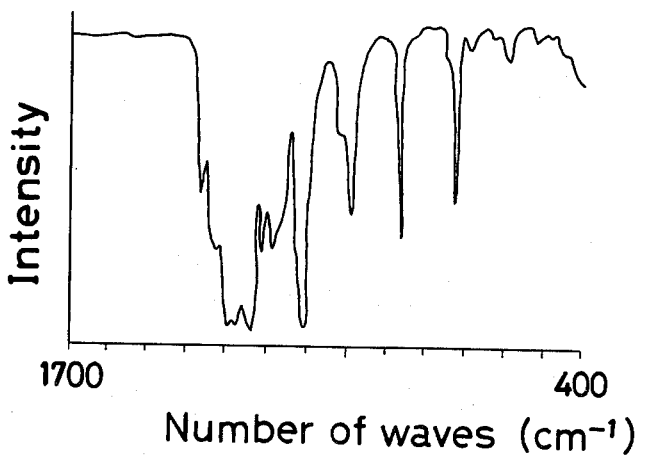

FIGS. 2 and 3 are infrared absorption spectra obtained of cis-perfluoro-(2,4-dimethyltetrahydrofuran) and trans-perfluoro-(2,4-dimethyltetrahydrofuran). In each chart, the vertical axis is graduated for intensity of infrared absorption and the horizontal axis for number of waves.

EXAMPLE 2

In the same cylindrical electrolytic cell that was used in Example 1, 1 liter of hydrofluoric acid was first introduced to be given preparatory electrolysis in the same way as in Example 1. Then, 0.244 mol of 2-ethyl-n-valeric acid methyl ester was dissolved therein. The resultant mixture was electrolyzed with 3.5 A/$dm^2$ of anodic current density, 5° to 6° C. of bath temperature over a period of 254 A.hr until the voltage reached 10 V.

The gas emanating from the electrolytic cell was treated in an iron tube packed with sodium fluoride pellets and in a gas scrubber bottle containing said mixed aqueous solution in much the same way as in Example 1. The gas emanating from the gas scrubber bottle was cooled with liquefied nitrogen. Thus, a total of 37.4 g of the product was collected in the cold trap. The liquid which remained inside the electrolytic cell separated into two layers, the upper layer consisting of hydrofluoric anhydride and the lower layer consisting of a substance containing high boiling fluorocarbons. The latter substance was separated and weighed. The amount was 34.2 g.

The product from the cooled trap and the liquid from the lower layer were refined by distillation and then subjected to analysis by gas chromatography, mass spectrometry, infrared absorption spectrometry and $^{19}F$ nuclear magnetic resonance spectrometry. It was consequently confirmed that the treatment afforded 5.1 g (5.9% in yield) of cis-perfluoro-(2-methyl-4-ethyltetrahydrofuran) (b.p. 75.4 to 75.7° C.) and 3.6 g (4.2% in yield) of trans-perfluoro-(2-methyl-4-ethyltetrahydrofuran) (b.p. 75.5° to 76° C.) as products aimed at, in conjunction with 8.4 g (9.8% in yield) of perfluoro-(2-ethyl-n-valeric acid fluoride), plus 4.0 g (4.7% in yield) of perfluoro-(3-n-propyltetrahydrofuran) and 2.0 g (2.4% in yield) of perfluoro-(3-ethyltetrahydropyran) as perfluoro-cyclic ethers.

FIGS. 4 and 5 represent infrared absorption spectra of cis-perfluoro-(2-methyl-4-ethyltetrahydrofuran) and trans-perfluoro-(2-methyl-4-ethyltetrahydrofuran) respectively.

EXAMPLE 3

In the same cylindrical electrolytic cell that was used in Example 1, 1 liter of hydrofluoric anhydride was placed and subjected to preparatory electrolysis by following the procedure of Example 1. Then, 0.202 mol of 2-n-propyl-n-valeric acid chloride was dissolved therein. The resultant mixture was electrolyzed with 3.5 A/$dm^2$ of anodic current density and 5° to 6° C. of bath temperature over a period of 213 A.hr until the voltage reached 10 V.

The gas emanating from the electrolytic cell was treated in an iron tube packed with sodium fluoride pellets and then in a scrubber bottle in much the same way as in Example 1. The gas from the scrubber bottle was cooled with liquid nitrogen and collected. The amount of the product thus collected was 16.6 g. The liquid which remained in the electrolytic cell separated into two layers, the upper layer consisting of hydrofluoric anhydride and the lower layer consisting of a substance containing high boiling fluorocarbons. The lower layer was separated and weighed. The amount was 31.0 g.

Figure 6:
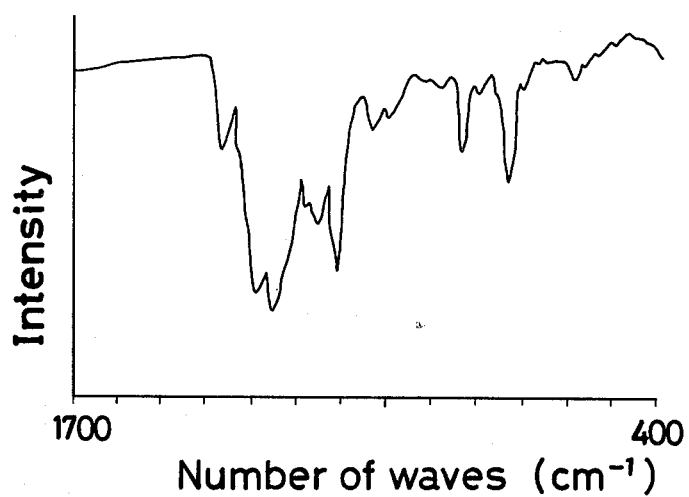
FIG. 6 is an infrared absorption spectrum of perfluoro-(2-methyl-4-n-propyltetrafuran) which was the product in Example 3.

The product from the cooled trap and the liquid from the lower layer were refined by distillation and then subjected to analysis by gas chromatography, mass spectrometry, infrared absorption spectrometry, and $^{19}F$ nuclear magnetic resonance spectrometry by following the procedure of Example 1. It was consequently ascertained that the treatment afforded 16.7 (19.9% in yield) of cis-trans mixture of perfluoro-(2-methyl-4-n-propyltetrahydrofuran) (b.p. 95.5° to 95.7° C.) as products aimed at, in conjunction with 5.6 g (6.7% in yield) of perfluoro-(2-n-propyl-n-valeric acid fluoride), plus 6.1 g (7.3% in yield) of perfluoro-(3-n-propyltetrahydropyran) as perfluoro-cyclic ether. FIG. 6 represents an infrared absorption spectrum of perfluoro-(2-methyl-4-n-propyltetrahydrofuran).

EXAMPLE 4

In the same cylindrical electrolytic cell that was used in Example 1, 1 liter of hydrofluoric anhydride was placed and subjected to preparatory electrolysis in much the same way as in Example 1. Then 0.202 mol of 2-n-butyl-n-caproic acid methyl ester was dissolved. The resultant mixture was electrolyzed with 3.5 A/dm² of anodic current density, 5° to 6° C. of bath temperature over a period of 283 A.hr until the voltage reached 10 V.

After the electrolysis, the liquid remaining inside the electrolytic cell separated into two layers, the upper layer consisting of hydrofluoric anhydride and the lower layer consisting of a substance containing high boiling fluorocarbons.

By opening the cock provided at the bottom of the electrolytic cell, said substance containing high boiling fluorocarbons was separated off from the upper layer. By weighing, the amount of the separated substance was found to be 54.0 g.

The separated substance was mixed with a small amount of molecular sieve 5 A pellets to have a small amount of entrained hydrogen fluoride removed by absorption. Then, it was refined by following the procedure of Example 1. By analysis resorting to gas chromatography, mass spectrometry, infrared absorption spectrometry and $^{19}F$ nuclear magnetic resonance spectrometry, it was confirmed that the treatment afforded 21.6 g (20.6% in yield) of cis-trans mixture of perfluoro-(2-ethyl-4-n-butyltetrahydrofuran) (b.p. 137° C. to 138.5° C.) as products aimed at, in conjunction with 13.4 g (12.8% in yield) of perfluoro-(2-n-butyl-n-caproic acid fluoride).

Figure 7:
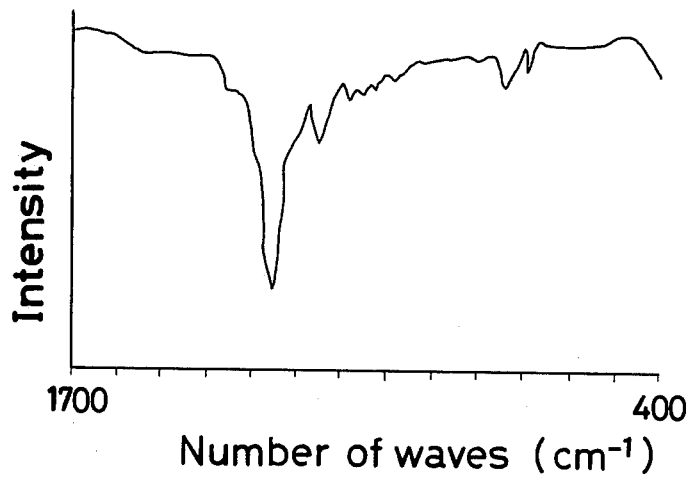
FIG. 7 is an infrared absorption spectrum of perfluoro-(2-ethyl-4-n-butyltetrahydrofuran) which was the product in Example 4.

FIG. 7 represents an infrared absorption spectrum of perfluoro-(2-ethyl-4-n-butyltetrahydrofuran).

What is claimed is:

1. A method for the manufacture of a perfluorotetrahydrofuran derivative represented by the generic formula:

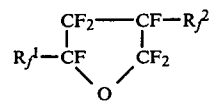

wherein $R_f^1$ is a member selected from the group consisting of a fluorine atom and straight-chain aliphatic perfluoroalkyl groups having 1 to 7 carbon atoms and $R_f^2$ is a straight-chain aliphatic perfluoroalkyl group having 1 to 7 carbon atoms, comprising the step of electrolyzing a member selected from the group consisting of a monocarboxylic acid and derivatives thereof represented by the generic formula:

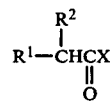

wherein the α carbon possesses side chains, $R^1$ and $R^2$ are each a straight-chain aliphatic alkyl group having 1 to 7 carbon atoms, X is a member selected from the group consisting of OH, halogens, $R^3O$ (where $R^3$ is a member selected from the group consisting of a methyl group and an ethyl group) and $NH_2$, and the total number of carbon atoms is not less than 6 and not more than 16, in a bath consisting essentially of hydrofluoric anhydride and having a temperature in the range of 0° C. to 10° C., at a voltage in the range of 4 V to 8 V and an anodic current density in the range of 2.0 A/dm² to 4.0 A/dm², while blowing helium gas into the bath.

2. The method according to claim 1, wherein the monocarboxylic acid or derivative thereof is a member selected from the group consisting of 2-methyl-n-valeric acid chloride, 2-methyl-n-caproic acid chloride, 2-methyl-n-enanthic acid chloride, 2-ethyl-n-valeric acid methyl ester, 2-n-propyl-n-valeric acid chloride, 2-ethyl-n-caproic acid chloride and 2-n-butyl-n-caproic acid methyl ester.

3. The method according to claim 1, wherein the perfluorotetrahydrofuran derivative is obtained by causing the gaseous reaction product issuing from the electrolysis to come into contact with sodium fluoride pellets for thereby removing hydrogen fluoride therefrom, then subjecting the effluent to a treatment with a gas scrubber for thereby removing therefrom hydrogen difluoride and carbonyl fluoride through absorption, cooling the remaining gas and subjecting the liquefied gas to further purification.

4. The method according to claim 1, wherein the perfluorotetrahydrofuran derivative is obtained by causing the lower of the two separate liquid layers produced after the electrolysis to be separated from the upper layer and subjecting the separated lower layer to purification.

* * * * *